United States Patent [19]

Marchetti

[11] 4,254,953
[45] Mar. 10, 1981

[54] ELBOW MOVEMENT RESTRICTER

[76] Inventor: Ralph D. Marchetti, 1040 Wayside Rd., Wayside, N.J. 07712

[21] Appl. No.: 33,398

[22] Filed: Apr. 26, 1979

[51] Int. Cl.$^3$ .......................... A63B 69/36; A63D 5/00
[52] U.S. Cl. ................................ 273/54 B; 273/183 B; 273/189 A; 128/77
[58] Field of Search ............ 273/189 R, 189 A, 54 B, 273/183 B; 272/132, 131, 119, DIG. 3; 128/77

[56] References Cited

U.S. PATENT DOCUMENTS

| | | | |
|---|---|---|---|
| 1,226,160 | 5/1917 | Allis | 273/189 A |
| 2,725,232 | 11/1955 | Magida | 272/132 |
| 3,099,448 | 7/1963 | Salvo et al. | 273/54 B |
| 3,350,100 | 10/1967 | Carmines | 273/189 R X |

*Primary Examiner*—George J. Marlo

*Attorney, Agent, or Firm*—Charles I. Brodsky

[57] ABSTRACT

The described apparatus is adapted to strap to the arm of a bowler or golfer to restrict the "breaking" of the player's elbow on making the bowling delivery or in completing the golf stroke so as to enable repetitive deliveries and/or strokes to be duplicative of one another for improved consistency of performance. The apparatus includes a pair of straps which encircle the user's arm above and below the elbow. The arm encircling straps are joined to each other by two pivotally connected sections, and the force required to move one section relative the other may be varied by a setscrew which passes through one section and bears against a land on the other section. Spaced apart pivot apertures in the pivotally connected sections enable such sections to be disassembled and then reassembled to each other at different pivot positions, to provide a size adjustment.

1 Claim, 3 Drawing Figures

U.S. Patent     Mar. 10, 1981     4,254,953
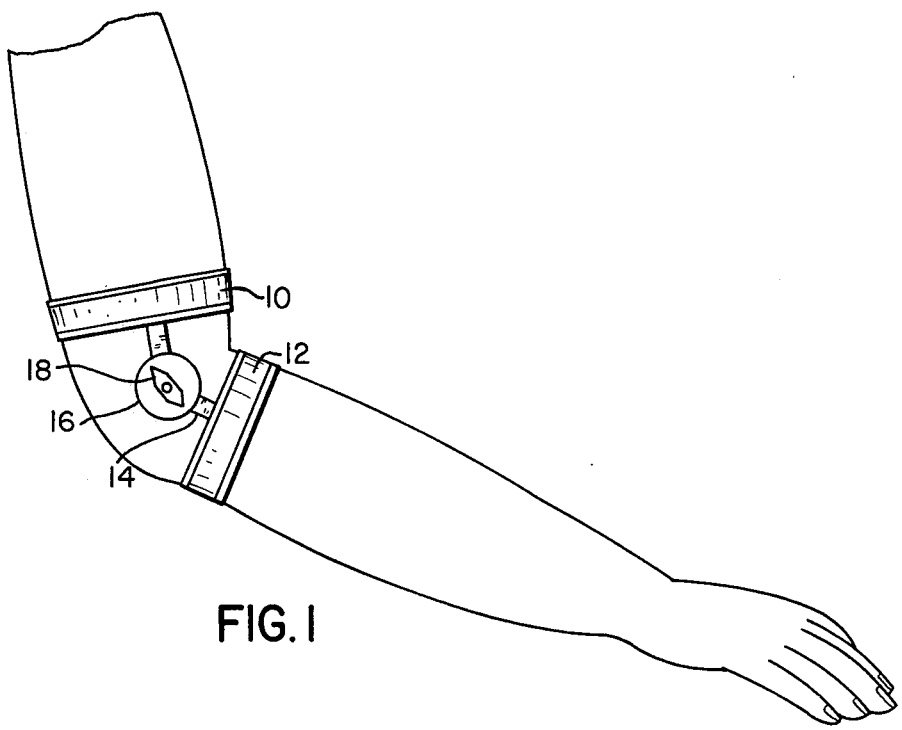
FIG. 1
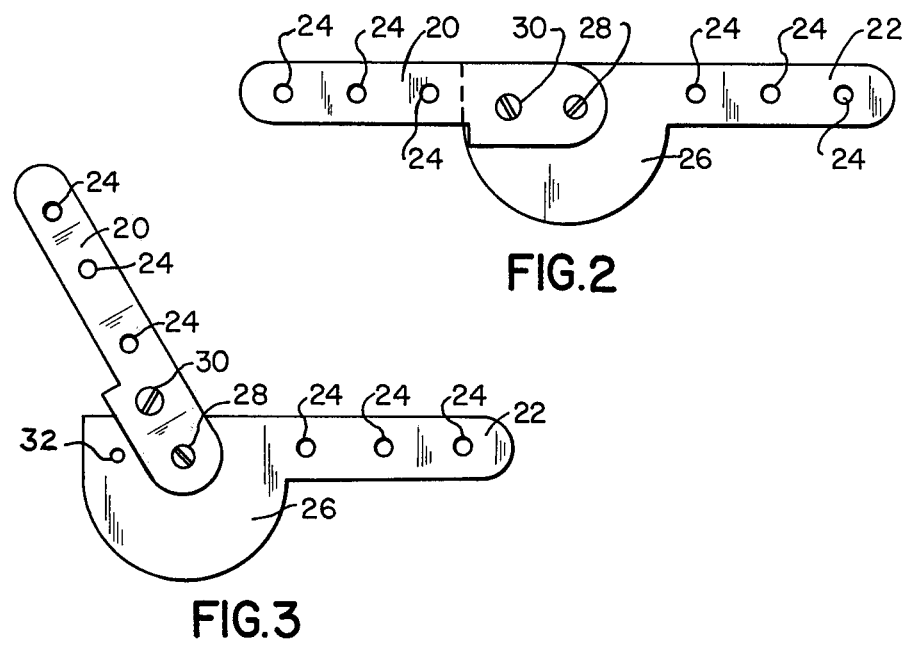
FIG. 2
FIG. 3

ELBOW MOVEMENT RESTRICTER

FIELD OF THE INVENTION

This invention relates to bowling and golf activities and, more particularly, to elbow movement restricting devices as are useful therein to enable repetitive arm motions to be duplicated with a substantial degree of consistency

BACKGROUND OF THE INVENTION

As is well known and understood, two of the most popular leisure time activities are bowling and golf. What with increasing television exposure, it is not unusual to find youngsters participating in these activities in one form or another, starting at the time that they enter school. Toy departments and toy stores almost always sell bowling games and golf sets for young children, because of the simplicity involved in rolling a ball at standing pins, or hitting a ball with a golf club. However, as these children get older and become adults, they quickly appreciate that the game of bowling and the game of golf are oftentimes very frustrating.

In particular, it is not uncommon to find a non-serious bowler burying the ball in the 1-2 or 1-3 pocket on one delivery, and only knocking down three or four of the ten pins on the next roll. Similarly, it is not unusual for a golfer to hit a perfect drive down the middle of a fairway, only to follow it up with a shank on the very next shot. Many times, after making such an improper roll, or improper stroke, the player laments "what did I do wrong?". Perhaps the more important question should be asked after the preceding roll or stroke, "what did I do right?".

As is also well known and appreciated various apparatus have been developed over the years in an attempt to aid the bowler and golfer in carrying out his delivery and swing in the manner most often taught by teaching professionals. With bowling aids, for example, a number of devices have been proposed to attempt to keep the wrist of the bowler under control—for example, to maintain the back of the hand in the same plane as the forearm. Devices for the golfer, however, have often proved cumbersome in their usage, to the extent that their acceptance by the amateur and professional alike have been many times less than the wide spread acceptance of bowling aids.

SUMMARY OF THE INVENTION

As will become clear hereinafter, the present invention describes a device useful both by the bowler and by the golfer to restrict the movement of his elbow in making a delivery of the bowling ball, or swinging the golf club. Experience has shown that for the amateur, especially, the amount of movement varies from one delivery to another, and from one swing to the next, amongst the same person. Analysis has shown that the vagaries between repeated actions has a drastic effect on the end result desired. Testing has indicated that by controlling the amount of movement, a duplication of efforts can result, such that each swing of the arm will be duplicative of the preceding and consistency of performance will result. As will be seen, the invention is adapted to fit along the arm, and adjacent to the elbow, to limit its movement, which can be controlled by a simple, and variable tension arrangement described.

BRIEF DESCRIPTION OF THE DRAWING

These and other features of the invention will be more clearly understood from a consideration of the following description, taken in accordance with the accompanying drawing in which:

FIG. 1 shows one form of elbow movement restricter constructed in accordance with the teachings of the invention;

FIG. 2 illustrates a second elbow movement restricting device according to the teachings herein; and FIG. 3 illustrates the elbow movement restricting device of FIG. 2 in a manner helpful to an understanding of the invention.

DETAILED DESCRIPTION OF THE DRAWING

The arrangement of FIG. 1 shows a pair of straps 10, 12 encircling the arm just above and below the elbow of a right-handed bowler. (For a right-handed golfer, on the other hand, it will be appreciated that the elbow control should be that on the left arm, and the arrangement of FIG. 1 will be understood to be there located.) A third strap 14 is included, connecting the straps 10, 12, and able to be tightened by a regulator 16 of variable tension control by means of a raised knob 18 which can be grasped and turned. For example, by turning the knob 18 in a clockwise direction as shown in the drawing, the strap 14 can be tightened in any acceptable manner and then locked in place. Conversely, the knob 18 can be rotated counter-clockwise, to reduce the tension on the strap 14, and then locked in place a second time. As will be appreciated, the knob 18 can be made continuously variable to adjust the tension over a wide range of degrees, or can be variable only in predetermined steps which, although permitting a lesser range of control, permits a more economical manufacture and design. With the degree of tension imparted, it will be apparent that the bending of the elbow can be regulated to an extent desired by the user, or by the teaching professional in developing the bowling or golf stroke of the player. As will be obvious to those skilled in the art, the straps 10, 12, can be closed in any appropriate manner so as to enable the device of the invention to rest firmly on the outside of the user's arm. With this configuration, elbow movement of the bowler and of the golfer can be restricted both during the back-swing and delivery (or down-swing) by substantially the same amount in each motion, and to permit essentially duplicative action on successive strokings. As will be readily acknowledged, it is the consistency of this action which the bowler or golfer desires to be present, in order that he may concentrate on the other aspects of the motion, and on its follow-through.

Whereas the apparatus of FIG. 1 is intended for use adjacent the elbow on the outside of the user's arm, the apparatus of FIG. 2 is configured to sit adjacent the elbow, but on the inside of the arm. In FIG. 2, a pair of extending arms 20, 22 are shown, each with an aperture 24 through which the arm encircling strap (not shown) extends in positioning the device on the arm. Depending upon the age of the user, the lengths of the extending arms 20, 22 can be of different size, to accommodate all potential wearers of this restricting device. Thus, understanding the intent of the extending arms to secure the device from the biceps area of the arm down to its forearm, the extending arms can be made of lengths of 1½, 3 and 4½ inches, respectively, for example, to provide devices of sizes "small", "medium", and "large".

As will be seen from FIG. 3, the extending arm 22 terminates in a semicircular land 26 of some 2-3 inches in diameter, and which in usage, sits adjacent the crook of the elbow, on the inside of the arm. The extending arm 20, on the other hand, is secured to the land 26 by means of a fastener pivot 28, so as to form, in essence, a hinge between the arms 20, 22.

Also shown in FIGS. 2 and 3 is a controllable means of varying the tension of the two arms 20, 22, and, more particularly, the ease with which the arms 20, 22 can rotate about the pivot 28. As shown in the drawing, such control means may comprise a set-screw 30 or other appropriate device arranged to extend through an aperture in the arm 20 so as to contact the near side of the land 26, as at the depression 32. With the arrangement illustrated, turning the set-screw 30 in a clockwise direction into the depression 32 serves to tighten the arms 20, 22, so as to resist any motion there-between. On the other hand, turning the set-screw 30 in a counter-clockwise direction out of the depression 32 releases the tightening afforded and permits the arms 20, 22 to rotate relative to one another about the pivot 28. With such an arrangement secured to the inner arm of the bowler (right arm of a right-handed bowler left arm of a right-handed golfer) the amount of elbow movement or break, can also be varied.

In the operation with these devices, the elbow movement is restricted such that the arm can be held straight, thus reducing one of the variables which tended to affect the bowling delivery or golf stroke. In manufacture, the extending arms of FIGS. 2 and 3 could be made from heavy guage aluminum, while the encircling straps of the drawing could be made of leather or any appropriate material with clamps made of Velcro or "hook-and-eye" type designs. The precise strap arrangements—i.e., the methods of their attachment and encirclement of the arm—are not critical to the design, as long as degrees of tension restraint can be controllable. In another version of the invention (not illustrated), the elbow movement restricters as are useful for control in bowling could be modified so as to permit some degree of elbow bending during the address position, which, however, rotate into a detented position during the bowler's back swing, and then controlled against further rotation during the delivery of the ball. As detent arrangements are well known in the field of mechanical fastening, any suitable arrangement could be utilized in such configuration. In any event, the controlled movement of the elbow that results will be repeated from delivery to delivery, and from swing to swing, so as to permit the bowler to roll his ball at his mark on the lanes in a more consistent manner, and to permit the arc of the golfer's swing to be duplicated during successive golf strokes, regardless of the club employed, and from the driver down through the putting stroke.

While there have been described what are considered to be preferred embodiments of the present invention, it will be readily appreciated by those skilled in the art that modifications may be made without departing from the scope of the teachings herein. For at least such reasons, therefore, reference should be had to the claims appended hereto for a proper understanding of the present invention.

I claim:

1. An elbow movement restricter for use by a bowler comprising:

first strap means adapted to encirle the upper arm of the bowler above the elbow, to be held in place thereat;

second strap means adapted to encircle the forearm of said bowler below the elbow, to be held in place thereat;

and means adapted to be positioned adjacent said elbow, interconnecting said first and second strap means, controllable to vary the tension thereof in restricting the movement of said first strap means relative to said second strap means during movement of the arm of said bowler to which said restricter is affixed;

wherein said interconnecting means is adapted to be positioned adjacent the elbow only on the inside position of the right arm of a right handed bowler, and adjacent the elbow only on the inside portion of the left arm of a left handed bowler;

wherein said interconnecting means incorporates a pair of extending arms coupled to respective ones of said first and second strap means and rotatable one about the other, and further incorporates means for continuously varying the tension between said pair of extending arms to controllably vary the relative movement between said strap means in maintaining substantially straight the elbow of the delivery arm of a bowler during the bowling motion;

wherein the one of said pair of extending arms which is coupled to said first strap means includes a semicircular land situate adjacent the crook of the bowler's elbow;

wherein the other of said pair of extending arms which is coupled to said second strap means is secured to said semicircular land by a pivot means so as to form a hinge therebetween; and wherein said tension varying means comprises screw means extending in a direction through said other of said pair of extending arms towards the land of said one of said pair of extending arms, and rotatable in clockwise and counterclockwise directions to controllably vary the relative movement between said pair of extending arms and between said first and second strap means to which said extending arms are coupled.

* * * * *